US00PP24856P2

(12) United States Plant Patent
Sakazaki

(10) Patent No.: US PP24,856 P2
(45) Date of Patent: Sep. 9, 2014

(54) ***TAGETES* PLANT NAMED '09TAG1002'**

(50) Latin Name: *Tagetes hybrida*
Varietal Denomination: 09TAG1002

(71) Applicant: Ushio Sakazaki, Hikone (JP)

(72) Inventor: Ushio Sakazaki, Hikone (JP)

(73) Assignee: Amerinova Properties LLC, Bonsall, CA (US)

( * ) Notice: Subject to any disclaimer, the term of this patent is extended or adjusted under 35 U.S.C. 154(b) by 7 days.

(21) Appl. No.: 13/815,880

(22) Filed: Mar. 15, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — C. A. Whealy

(57) ABSTRACT

A new and distinct cultivar of *Tagetes* plant named '09TAG1002', characterized by its compact, upright and mounding; vigorous growth habit; freely flowering habit; long flowering period; and daisy-type inflorescence form with broad golden yellow-colored ray florets.

1 Drawing Sheet

Botanical designation: *Tagetes hybrida.*
Cultivar denomination: '09TAG1002'.

BACKGROUND OF THE INVENTION

The present invention relates to a new and distinct cultivar of *Tagetes* plant, botanically known as *Tagetes hybrida*, and hereinafter referred to by the name '09TAG1002'.

The new *Tagetes* plant is a product of a planned breeding program conducted by the Inventor in Higashiomi, Shiga, Japan. The objective of the breeding program is to create new long-flowering *Tagetes* plants with large showy inflorescences.

The new *Tagetes* plant originated from a cross-pollination conducted by the Inventor in Higashiomi, Shiga, Japan on May 10, 2008 of a unnamed proprietary seedling selection of *Tagetes lemmonii*, not patented, as the female, or seed, parent with an unidentified seedling selection of *Tagetes hybrida* as the male, or pollen, parent. The new *Tagetes* plant was discovered and selected by the Inventor as a single flowering plant from within the progeny of the stated cross-pollination in a controlled greenhouse environment in Higashiomi, Shiga, Japan on Jun. 18, 2009.

Asexual reproduction of the new *Tagetes* plant by vegetative cuttings since Jun. 20, 2009 in a controlled greenhouse environment in Higashiomi, Shiga, Japan, has shown that the unique features of this new *Tagetes* plant are stable and reproduced true to type in successive generations.

SUMMARY OF THE INVENTION

Plants of the new *Tagetes* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of '09TAG1002'. These characteristics in combination distinguish '09TAG1002' as a new and distinct *Tagetes* plant:

1. Compact, upright and mounding.
2. Vigorous growth habit.
3. Freely flowering habit.
4. Long flowering period.
5. Daisy-type inflorescence form with broad golden yellow-colored ray florets.

Plants of the new *Tagetes* differ primarily from plants of the female parent selection in the following characteristics:

1. Inflorescences of plants of the new *Tagetes* have broader ray florets than inflorescences of plants of the female parent selection.
2. Plants of the new *Tagetes* flower for a longer period of time than plants of the female parent selection.

Plants of the new *Tagetes* differ primarily from plants of the male parent selection in the following characteristics:

1. Plants of the new *Tagetes* are much more vigorous than plants of the male parent selection.
2. Leaves of plants of the new *Tagetes* have a pleasant fragrance whereas leaves of plants of male parent selection have an unpleasant fragrance.
3. Plants of the new *Tagetes* are more disease-tolerant than plants of the male parent selection.

Plants of the new *Tagetes* can be compared to plants of other selections of *Tagetes hybrida* known to the Inventor. In side-by-side comparisons conducted in Higashiomi, Shiga, Japan, plants of the new *Tagetes* differed from plants of the known selections in the following characteristics:

1. Plants of the new *Tagetes* were more vigorous than plants of the known selections.
2. Plants of the new *Tagetes* flowered for a longer period of time than plants of the known selections.
3. Plants of the new *Tagetes* were more disease tolerant than plants of the known selections.

BRIEF DESCRIPTION OF THE PHOTOGRAPHS

The accompanying photographs illustrate the overall appearance of the new *Tagetes* plant showing the colors as true as it is reasonably possible to obtain in colored reproductions of this type. Colors in the photographs may differ slightly from the color values cited in the detailed botanical description which accurately describe the colors of the new *Tagetes* plant.

The photograph at the bottom of the sheet comprises a side perspective view of typical flowering plant of '09TAG1002' grown in a container.

The photograph at the top of the sheet is a close-up view of a typical flowering plant of '09TAG1002'.

DETAILED BOTANICAL DESCRIPTION

The aforementioned photographs and following observations and measurements describe plants grown during the autumn in one-gallon containers in a polyethylene-covered greenhouse in Bonsall, Calif. and under cultural practices typical of commercial *Tagetes* production. During the production of the plants, day temperatures ranged from 20° C. to 29° C. and night temperatures ranged from 7° C. to 18° C. Plants were pinched one time at planting. Plants were five weeks old when the photographs and description were taken. In the following description, color references are made to The Royal Horticultural Society Colour Chart, 2007 Edition, except where general terms of ordinary dictionary significance are used.

Botanical classification: *Tagetes hybrida* '09TAG1002'.

Parentage:

*Female, or seed, parent*.—Unnamed proprietary seedling selection of *Tagetes lemmonii*, not patented.

*Male, or pollen, parent*.—Unidentified seedling selection of *Tagetes hybrida*, not patented.

Propagation:

*Type*.—By vegetative cuttings.

*Time to initiate roots*.—About one week.

*Time to produce a rooted young plant*.—About two weeks.

*Root description*.—Fine, fleshy; white in color.

*Rooting habit*.—Moderately freely branching; dense.

Plant description:

*Plant and growth habit*.—Compact, upright and mounding plant habit; inverted triangular plant form; freely branching habit with about ten primary branches with secondary laterals potentially developing at every node; bushy appearance; inflorescences held above the foliar plane on wiry peduncles; vigorous growth habit.

*Plant height*.—About 14 cm.

*Plant diameter or spread*.—About 17.5 cm.

*Lateral branches*.—Length: About 10.5 cm. Diameter: About 1.5 cm. Internode length: About 2.8 cm. Texture: Sparsely pubescent. Strength: Moderately strong, wiry. Color: Close to 144A.

Leaf description:

*Arrangement and shape*.—Alternate, simple but deeply dissected with three to five lobes.

*Length*.—About 2.7 cm.

*Width*.—About 2.4 cm.

*Apex*.—Acute.

*Base*.—Attenuate.

*Margin*.—Serrulate; sinuses parallel.

*Venation pattern*.—Pinnate.

*Texture, upper and lower surfaces*.—Smooth, glabrous.

*Fragrance*.—Strong, pleasant.

*Color*.—Developing leaves, upper surface: Close to 137B. Developing leaves, lower surface: Close to 146B. Fully expanded leaves, upper surface: Close to 137A; venation, close to 147B. Fully expanded leaves, lower surface: Close to 147B; venation, close to 147AC.

*Petioles*.—Length: About 6 mm. Diameter: About 1 mm. Texture, upper and lower surfaces: Smooth, glabrous. Color, upper surface: Close to 146C. Color, lower surface: Close to 147B.

Inflorescence description:

*Appearance and flowering habit*.—Rotate daisy-type inflorescences with ray and disc florets developing acropetally on a receptacle; inflorescences terminal or axillary and positioned above and beyond the foliar plane on wiry peduncles; inflorescences face mostly upright to outwardly; freely flowering habit with typically about six inflorescences developing per lateral branch.

*Fragrance*.—Strongly fragrant, sour; typical of *Tagetes*.

*Time to flower*.—Plants begin flowering about five weeks after planting; flower continuously from the spring into the autumn in Southern California.

*Post-production longevity*.—Inflorescences maintain good substance for about three days on the plant; inflorescences persistent.

*Inflorescence buds*.—Height: About 1.4 cm. Diameter: About 6 mm. Shape: Slender, elongate. Color: Close to 153D.

*Inflorescence diameter*.—About 2.7 cm.

*Inflorescence depth* (*height*).—About 1.8 cm.

*Disc diameter*.—About 6 mm.

*Receptacle height*.—About 1.2 cm.

*Receptacle diameter*.—About 4 mm.

*Receptacle color*.—Close to 137B.

*Ray florets*.—Length: About 1.7 cm. Width: About 1 cm. Shape: Obovate to slightly obcordate. Apex: Shallowly emarginate. Base: Attenuate. Margin: Entire. Aspect: Initially upright to roughly perpendicular to the peduncle; reflexing with development. Texture, upper and lower surfaces: Smooth, glabrous; velvety. Number of ray florets per inflorescence: About five or six arranged in a single whorl. Color: When opening, upper surface: Close to 21A to 21B. When opening, lower surface: Close to 13A to 13B. Fully opened, upper surface: Close to 17A; color does not fade with development. Fully opened, lower surface: Close to 15A; color does not fade with development.

*Disc florets*.—Shape: Tubular, slender; apex dentate. Length: About 1.6 cm. Diameter: About 1.5 mm. Number of disc florets per inflorescence: About 22 massed at the center of the receptacle. Color, immature: Apex: Close to 153D. Mid-section: Close to 5B. Base: Close to 145D. Color, mature: Apex: Close to 17B. Mid-section: Close to 15A. Base: Close to 199A.

*Phyllaries*.—Quantity per inflorescence: About five to six arranged in a single campanulate tube. Length: About 1 cm. Width: About 1.5 mm. Shape: Lanceolate. Apex: Acute. Margin: Free apices are entire, ciliate. Texture, inner surface: Smooth, glabrous. Texture, outer surface: Scattered pubescence. Color, inner surface: Close to 146C. Color, outer surface: Close to 146A to 146B.

*Peduncles*.—Length, terminal peduncle: About 3.5 cm. Length, second peduncle: About 4.4 cm. Length, third peduncle: About 5.8 cm to 6.2 cm. Diameter: About 1 mm. Strength: Moderately strong. Texture: Smooth, glabrous; wiry. Color: Close to 137A.

*Reproductive organs*.—Androecium, present on disc florets only: Quantity per disc floret: Five. Filament length: About 6 mm. Filament color: Close to 145D. Anther shape: Lanceolate. Anther length: About 2.5 mm. Anther color: Close to 22A. Pollen amount: Scarce. Pollen color: Close to 22A. Gynoecium, present on ray and disc florets: Quantity per floret: One. Pistil length: About 1.6 cm. Stigma shape: Biparted and reflexing. Stigma color: Close to 23A. Style length: About 9 mm. Style color: Close to 145C. Ovary color: Close to 199B to 199C. Fruits and seeds: Fruit and seed development have not been observed on plants of the new *Tagetes*.

Disease tolerance: Plants of the new *Tagetes* have been shown to be more tolerant to most pathogens common to *Tagetes* plants than other selections of *Tagetes* known to the Inventor.

Garden performance: Plants of the new *Tagetes* have exhibited good tolerance to rain and wind and have been observed to tolerate temperatures from about 1° C. to about 35° C.

It is claimed:

1. A new and distinct *Tagetes* plant named '09TAG1002' as illustrated and described.

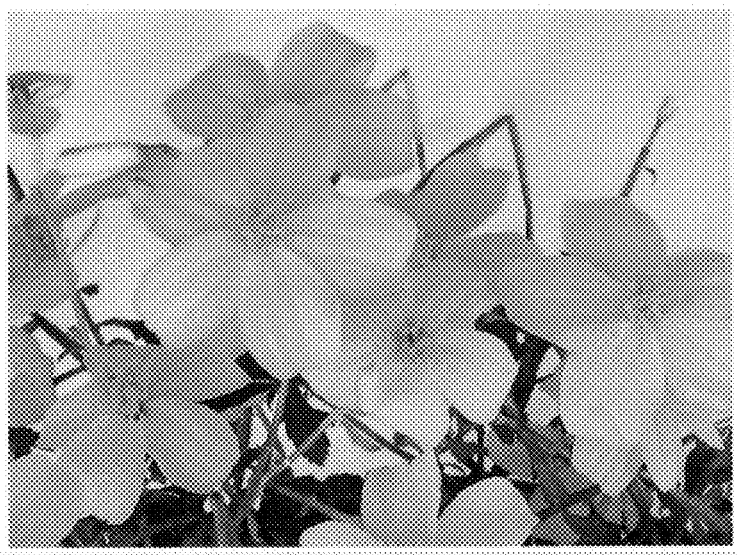
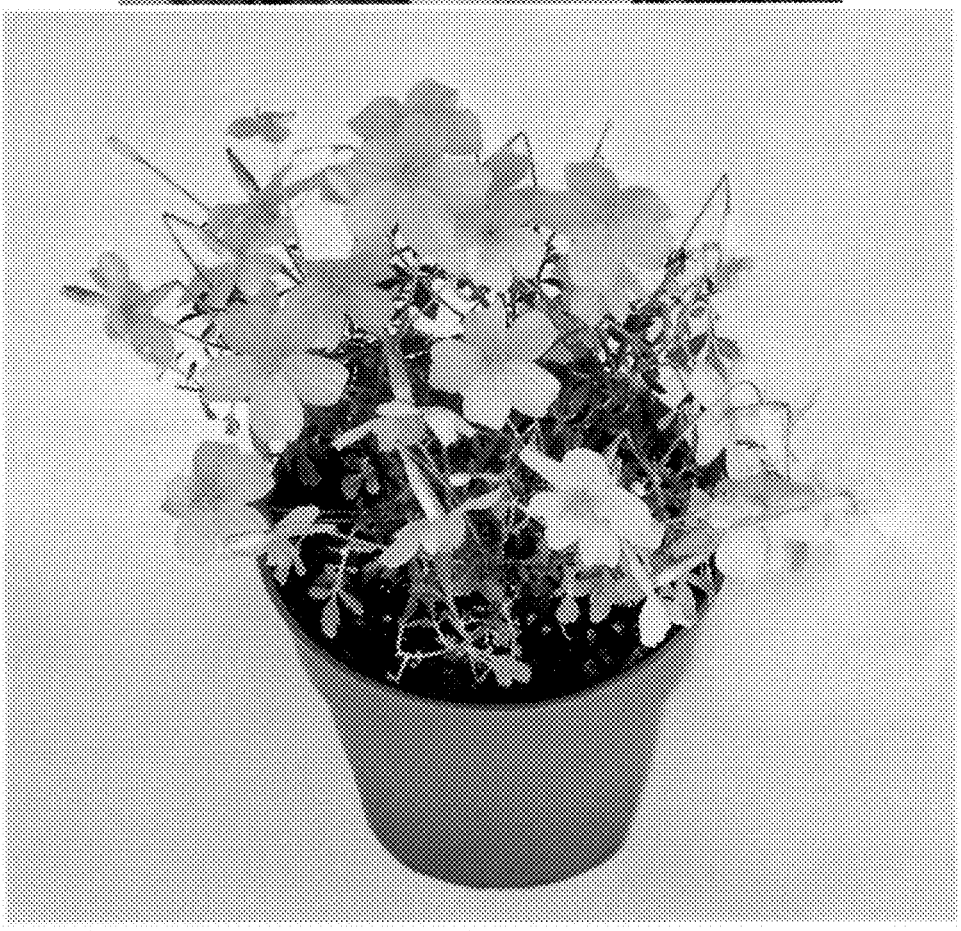

* * * * *